(12) United States Patent
Ikeda et al.

(10) Patent No.: US 8,431,907 B2
(45) Date of Patent: Apr. 30, 2013

(54) PARTICLE BEAM TREATMENT DEVICE AND IRRADIATION DOSE SETTING METHOD OF THE PARTICLE BEAM TREATMENT DEVICE

(75) Inventors: Masahiro Ikeda, Tokyo (JP); Hisashi Harada, Tokyo (JP); Osamu Takahashi, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 47 days.

(21) Appl. No.: 13/318,866

(22) PCT Filed: Mar. 8, 2011

(86) PCT No.: PCT/JP2011/055347
§ 371 (c)(1),
(2), (4) Date: Nov. 4, 2011

(87) PCT Pub. No.: WO2012/120636
PCT Pub. Date: Sep. 13, 2012

(65) Prior Publication Data
US 2012/0313002 A1    Dec. 13, 2012

(51) Int. Cl.
*G01J 1/42* (2006.01)
*A61N 5/00* (2006.01)
*G21G 5/00* (2006.01)

(52) U.S. Cl.
USPC ............... 250/393; 250/492.1; 250/492.2; 250/492.3

(58) Field of Classification Search ............ 250/492.1, 250/492.2, 492.3, 393
See application file for complete search history.

(56) References Cited

U.S. PATENT DOCUMENTS 6,891,177 B1 * 5/2005 Kraft et al. ............... 250/505.1
7,102,144 B2 * 9/2006 Matsuda et al. ........... 250/492.1
(Continued)

FOREIGN PATENT DOCUMENTS
JP    7-136290 A     5/1995
JP   10-314323 A    12/1998
(Continued)

OTHER PUBLICATIONS

International Search Report (PCT/ISA/210) issued on Apr. 19, 2011, by Japanese Patent Office as the International Searching Authority for International Application No. PCT/JP2011/055347.
(Continued)

*Primary Examiner* — David Porta
*Assistant Examiner* — Kenneth J Malkowski
(74) *Attorney, Agent, or Firm* — Buchanan Ingersoll & Rooney PC

(57) ABSTRACT

A particle beam treatment device includes an irradiation nozzle which moves a particle beam in a direction which is perpendicular to an advancing direction; a dose monitor which measures the dose of the particle beam; a planning part which sets the irradiation dose applied to a target volume; and a controlling part which controls the irradiation dose applied to a target volume based on irradiation dose set value which is set by a value measured by the dose monitor and the planning part, wherein the planning part stores the absorbed dose distribution data in the depth direction which is prepared in advance using the absorbed dose at the reference depth which is a predetermined position nearer to an incident side of the particle beam than the position of Bragg peak as the reference and calculates the irradiation dose set value using the absorbed dose at the reference depth.

12 Claims, 16 Drawing Sheets

U.S. PATENT DOCUMENTS

| | | |
|---|---|---|
| 2004/0227104 A1 | 11/2004 | Matsuda et al. |
| 2009/0060130 A1 | 3/2009 | Wilkens et al. |
| 2009/0283702 A1* | 11/2009 | Umezawa et al. ......... 250/492.3 |
| 2011/0012028 A1 | 1/2011 | Harada et al. |

FOREIGN PATENT DOCUMENTS

| | | |
|---|---|---|
| JP | 2004-358237 A | 12/2004 |
| JP | 2008-245716 A | 10/2008 |
| JP | 2008-253496 A | 10/2008 |
| JP | 2009-525797 A | 7/2009 |
| WO | WO 2009/139043 A1 | 11/2009 |

OTHER PUBLICATIONS

Written Opinion (PCT/ISA/237) issued on Apr. 19, 2011, by Japanese Patent Office as the International Searching Authority for International Application No. PCT/JP2011/055347.

* cited by examiner

| ENERGY | ENERGY CORRECTION COEFFICIENT |
|---|---|
| REFERENCE ENERGY | 1.00 |
| ENERGY A | 1.12 |
| ENERGY B | 1.23 |
| ENERGY C | 1.35 |
| ⋮ | ⋮ |
| ENERGY N | 1.95 |

PARTICLE BEAM TREATMENT DEVICE AND IRRADIATION DOSE SETTING METHOD OF THE PARTICLE BEAM TREATMENT DEVICE

TECHNICAL FIELD

This invention relates to a particle beam treatment device which performs the treatment of cancer by radiating a particle beam, especially to an irradiation dose setting method.

BACKGROUND ART

The treatment of a cancer is one of applications of radiation beam. Recently, particle beam treatment in which a particle beam such as a proton beam or a carbon beam is radiated on the cancer cell has been attracted attention. First of all, the characteristic of a particle beam radiation in which the particle beam is radiated to kill a cancer cell will be described. In a case where various kinds of radiation beams are radiated on a human body, the dose distribution of the radiation beam in the human body changes as shown in FIG. 18. As shown in FIG. 18, among various kinds of radiations, a photon beam such as an X-ray or a gamma ray has a relative dose which becomes maximum in a portion close to the surface of the body, and is decreased as the depth from the surface of the body is increased. On the other hand, a particle beam, such as a proton beam or a carbon beam, has a relative dose which has a peak value at a position where the beam stops at a deep portion from the surface of the body, that is, immediately before the range of the particle beam. This peak value is called the Bragg Peak (BP).

Particle beam cancer treatment is such that this Bragg peak BP is radiated to a tumor formed in a human organ and the treatment of the cancer is performed. In addition to the cancer, it can also be used for a case where a deep portion of a body is treated. A region to be treated, including a tumor, is generally called a target volume (TV). The position of the Bragg peak BP is determined by the energy of an radiated particle beam, and as the energy of the particle beam becomes high, the Bragg peak BP is formed at a deep position. In the particle beam treatment, it is necessary that the particle beam is made to have a uniform dose distribution over the whole of the target volume to be irradiated. In order to give the Bragg peak BP to the whole region of the target volume, "spread of an irradiation volume" of the particle beam is performed.

This "spread of an irradiation volume" is performed in three directions of an X-axis, a Y-axis and a Z axis perpendicular to each other. When the irradiation direction of the particle beam is set to be the direction of the Z-axis, "spread of an irradiation volume" is first performed so as to spread the irradiation field in the X-axis and Y-axis directions, and since the irradiation field spread is performed in the lateral direction perpendicular to the depth direction, it is generally called the irradiation field spread. The second "spread of an irradiation volume" is such that the irradiation volume spread is performed in the Z-axis, and it is called the irradiation volume spread in the depth direction.

The irradiation volume spread in the depth direction is performed to spread the Bragg peak BP, which is in the irradiation direction of the particle beam, to the depth direction since the width of the Bragg peak BP in the irradiation direction of the particle beam is narrow as compared with the extent of the target volume in the depth direction. On the other hand, the irradiation field spread in the lateral direction is performed to spread the irradiation field in the Bragg peak BP in the direction perpendicular to the irradiation direction since the diameter of the particle beam, which is accelerated by an accelerator generally, is smaller than the size of the target volume in the direction perpendicular to the irradiation direction. With respect to the irradiation volume spread in the depth direction and the irradiation field spread in the lateral direction, various kinds of methods have been proposed so far. Recently, Scanning Irradiation method has attracted attention.

In Scanning Irradiation method, as an irradiation field spread method in a lateral direction, there is a method in which a deflection electromagnet provided at the upstream portion of a particle beam irradiation part of a particle beam treatment device is used to scan the particle beam which is formed at a pencil beam having a small diameter in the XY plane, and the irradiation position of the particle beam is moved with the lapse of time to obtain a wide irradiation field. In this method, a uniform dose distribution can be obtained by suitably overlapping adjacent irradiation spots of small diameter pencil beams. Scanning methods of a pencil beam include a raster method of performing scanning continuously with respect to time, and a spot method of performing a step-like scanning with respect to time.

As the irradiation volume spread method in the depth direction, there is a method in which the energy of the particle beam itself which is radiated from a particle beam treatment device is controlled. In this method, the energy of the particle beam is controlled by changing the acceleration energy of an accelerator which accelerates the particle beam, or the energy of the particle beam is changed by inserting a tool called a range shifter so as to cross the particle beam. There is also a method in which both the control by the accelerator and the range filter are used.

In the irradiation volume spread method in the depth direction, the particle beam is made to be the beam having the energy of specified intensity, after one of irradiation layers of a target volume TV is irradiated with the Bragg peak BP with a uniform dose, the energy of the particle beam is changed, and next irradiation layer of the target volume TV is irradiated with the Bragg peak BP. Such operation is repeated plural times so as for plural irradiation layers to be irradiated with the Bragg peak BP of the particle beam. Consequently, the spread-out Bragg peak SOBP having a desired width in the beam irradiation direction can be obtained.

A particle beam irradiation method in which the irradiation field spread method in lateral direction and the irradiation volume spread method in depth direction are combined is the Scanning Irradiation method.

In the Scanning Irradiation method, the target irradiation dose at an irradiation position is set by a treatment plan. The shape of irradiation field and target irradiation dose for each irradiation position depends on patients. Two kinds of dose are defined, that is, physical dose and biological dose (also referred to as biology dose and effective dose). Physical dose is energy per mass which is applied to a part having a target, and its unit is gray (Gy). On the other hand, biology dose is a value which is determined based on the physical dose in consideration of biological influence to a cell, and its unit is gray equivalent (GyE). The biology dose is defined by the condition, for example, the dose which is equivalent to the irradiation dose by cobalt 60 which makes the survival ratio of cell to be 10%. In particle beam treatment, prescription dose is defined by the biology dose. The aim of the irradiation volume spread is to make uniform the irradiation effect, and targeted dose for every patient is defined by biology dose distribution. On the other hand, by the dose monitor which is used for measuring the administration dose, the biological effect can not be measured, therefore dose calibration is performed by using the physical dose.

In particle beam treatment, it is necessary for a biology dose distribution in a target volume TV of a particle beam to be actually irradiated according to the distribution which is set in treatment plan. On the other hand, there is not any method to measure directly the biology dose in the target volume TV during irradiation. Further, with respect to outside of an affected part, only the physical dose can be measured during irradiation. Accordingly, irradiation should be applied so as to make the biology dose in a target volume TV to be a value which is set by a treatment plan while controlling the physical dose.

Therefore, the step of dose calibration is performed before irradiation, however, in the prior arts, only at one point of center of SOBP in the depth-direction distribution of biology dose, dose calibration is performed. For example, in Patent Document 1, it is disclosed such that "the target is split into a plurality of layers, and an irradiation amount for every layer is determined". In Patent Document 2, it is disclosed such that "the target is split into a plurality of layers, and an irradiation amount for each layer is determined so as to be uniform".

According to the technology described in Patent Document 1 or Patent Document 2, since the change of Bragg curves in the depth direction is steep, a large error is caused by a slight position error with respect to the position for setting a dose meter. As the technology for solving the above-mentioned problems, in Patent Document 3, the technology for reducing the position error by forming a flat area in a peak of Bragg curves.

Prior Art References

Patent Document

Patent Document 1: Patent Application Laid-Open No. 2004-358237

Patent Document 2: Patent Application Laid-Open No. 10-314323

Patent Document 3: National Publication of International Patent Application No.2009-139043A1

DISCLOSURE OF THE INVENTION

Problems to be Solved by The Invention

Irradiation methods of a particle beam described in Patent Document 1, 2 and 3 regard to the broad beam irradiation methods in which beams are spread laterally and dose distribution which is laterally-uniform is formed so as to irradiate. Consequently, the above-mentioned technology can not be directly applied to the scanning irradiation method in which pencil beams having the Gaussian distribution are superimposed so as to irradiate.

Regarding a particle beam treatment device in accordance with scanning irradiation method in which pencil beams having the Gaussian distribution are superimposed so as to irradiate, this invention aims to obtain a particle beam treatment device in which appropriate dose calibration can be performed.

Means for Solving the Problems

This invention provides a particle beam treatment device comprising an irradiation nozzle for radiating a particle beam as a pencil beam to a target volume so as to form a spot of the particle beam which is the maximum adsorption region at a position in the depth direction of a target volume which is determined by the energy of the particle beam, and for radiating a particle beam to a target volume by moving the pencil beam in the lateral direction which is perpendicular to the advancing direction so as to move the position of the spot in the lateral direction; a dose monitor which measures the dose of a particle beam which is emitted from the irradiation nozzle; a treatment planning part which sets the irradiation dose set value which is applied to a target volume; and a treatment control part having an energy setting controller which sets the energy of a particle beam, a beam scanning controller which controls the irradiation nozzle and an irradiation dose controller which controls the irradiation dose which is applied to a target volume based on the measurement value of the dose monitor and an irradiation dose set value which is set by the treatment planning part, wherein the treatment planning part stores PDD which is the absorbed dose distribution data in the depth direction which is prepared in advance by using the absorbed dose at the reference depth which is a predetermined position and nearer to an incident side of the pencil beam than the position of a Bragg peak as the reference, and an irradiation dose set value which is calculated by using an absorbed dose at the reference depth as the reference is outputted to the irradiation dose controller.

Further, the irradiation dose setting method of the particle beam treatment device according to this invention includes a step of storing PDD which is absorbed dose distribution data in the depth direction which is prepared in advance at plural energy of particle beam by using (the) absorbed dose at the reference depth which is a predetermined position which is nearer to an incident side of the pencil beam than the position of a Bragg peak as the reference, and a step of calculating an irradiation dose set value based on the PDD which is stored by using the absorbed dose at the reference depth as the reference.

Advantage of the Invention

In a particle beam treatment device in accordance with a scanning irradiation method, by using an absorbed dose which has less change in the depth direction as reference, an irradiation dose set value is calculated. Consequently, appropriate dose calibration can be performed.

EMBODIMENTS FOR CARRYING OUT THE INVENTION

Embodiment 1

Figure 1:
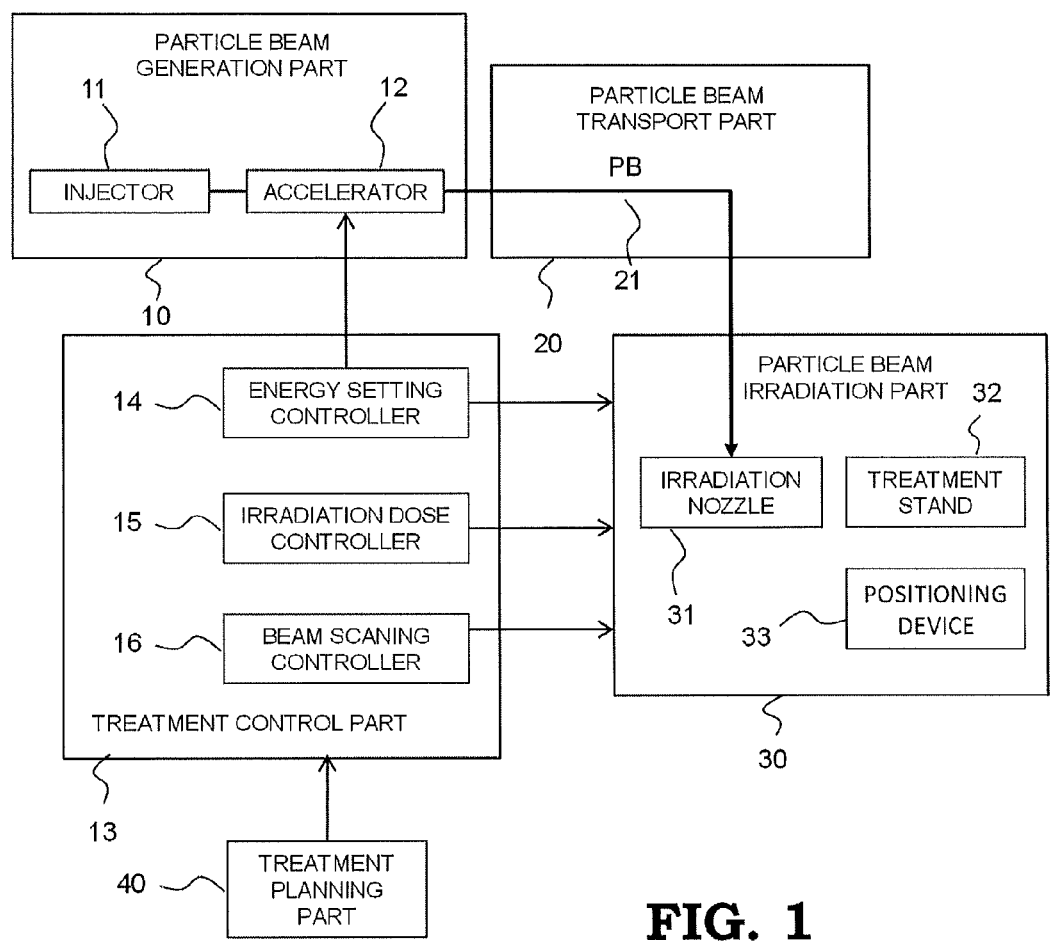
FIG. 1 is a block diagram schematically illustrating the configuration of a particle beam treatment device according to the present invention.
Figure 2:
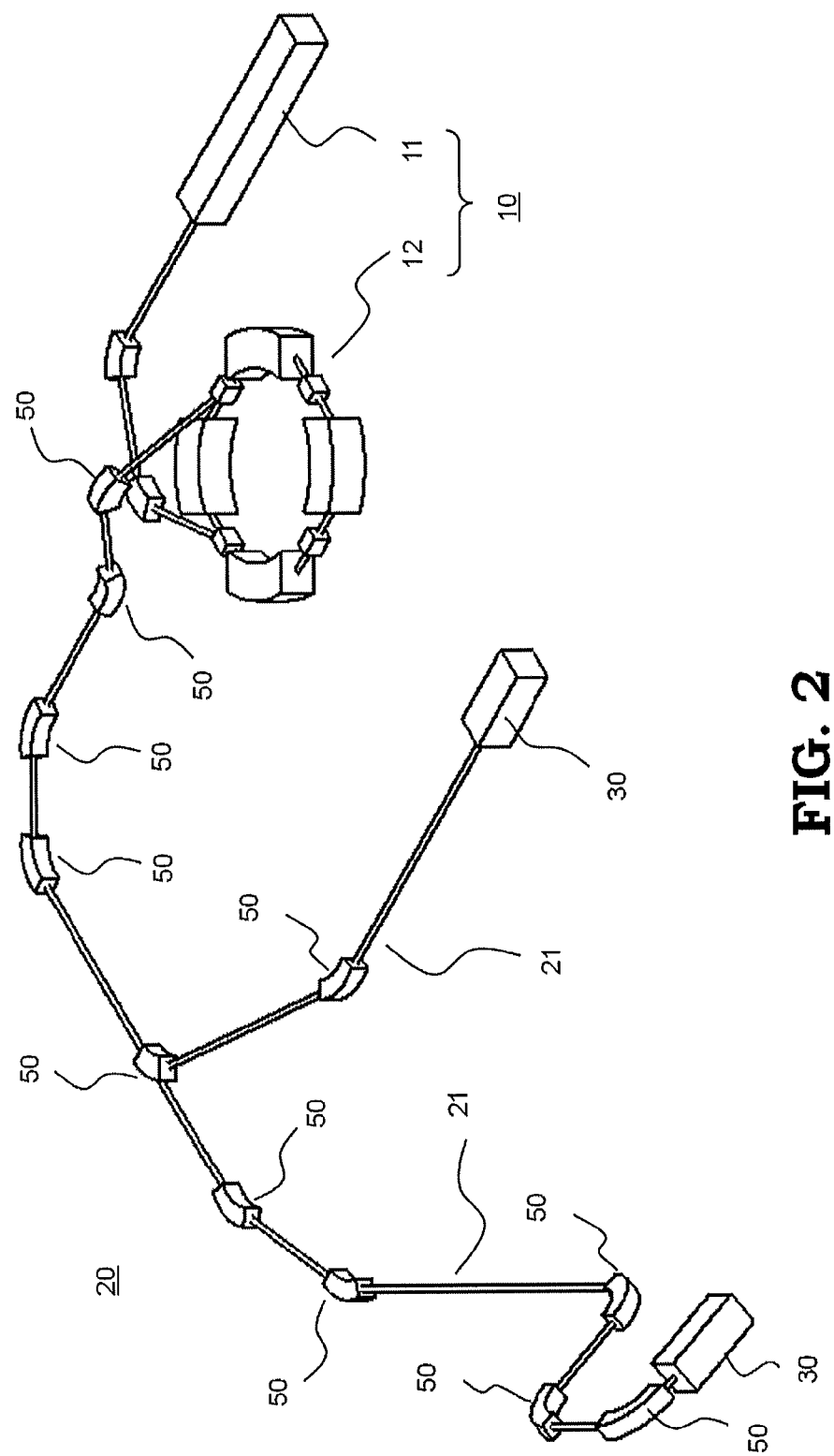
FIG. 2 is a bird's-eye view schematically illustrating an example of whole configuration of a particle beam treatment device to which the present invention is applied.

FIG. 1 is a block diagram schematically illustrating the configuration of a particle beam treatment device according to the present invention and FIG. 2 is a bird's-eye view schematically illustrating an example of whole configuration of a particle beam treatment device. As shown in FIGS. 1 and 2, the particle beam treatment device includes a particle beam generation part 10, a particle beam transport part 20, and two particle beam irradiation parts 30. FIG. 2 shows a particle beam treatment device having two particle beam irradiation parts, however, number of particle beam irradiation part is not limited to two, a particle beam treatment device having one particle beam irradiation part or three or more particle beam irradiation parts may be acceptable. For simplification, FIG. 1 shows a particle beam treatment device having one particle beam irradiation part. For reasons of application of radiation safety management and the like, the particle beam generation part 10 and the particle beam irradiation part 30 are installed in individual shielded rooms. The particle beam transport part 20 connects the particle beam generation part 10 to the particle beam irradiation part 30. The particle beam transport part 20 includes a particle beam transport passage 21 to transport a particle beam generated in the particle beam generation part 10 to the particle beam irradiation parts 30. The particle beam transport part 20 has a deflection electromagnet 50 for changing the direction of a particle beam and is constructed so as for a particle beam to pass through a vacuum duct. The particle beam irradiation part 30 is configured such that a target volume of a patient is irradiated with a particle beam PB.

The particle beam generation part 10 includes an injector 11 and an accelerator 12. The injector 11 generates a particle beam such as a proton beam or a carbon beam. The accelerator 12 accelerates the particle beam generated in the injector 11, and forms a particle beam PB. Accelerators include a synchrotron, a cyclotron, etc. The accelerator 12 electrically connects to an energy setting controller 14 provided in a treatment control part 13. The energy setting controller 14 supplies an energy setting signal to the accelerator 12 and sets the accelerating energy so as to set and control the energy of particle beam PB emitted from the accelerator 12. Consequently, the energy setting controller 14 controls the irradiation volume spread in the depth direction, that is, the irradiation position of a particle beam in the depth direction. The energy setting controller 14 generally sets the energy of a particle beam based on the data which is received by a treatment planning part 40 so as to control to overlap plural irradiation layers having different ranges in the depth direction. The energy of a particle beam is changed for each irradiation layer and a spread out Bragg peak SOBP is formed in the irradiation direction of a particle beam PB, that is, in the Z-axis direction. The treatment control part 13 sets the irradiation dose in treatment, and has an irradiation dose controller 15 to control the particle beam generation part 10 and the particle beam irradiation part 30.

Figure 3:
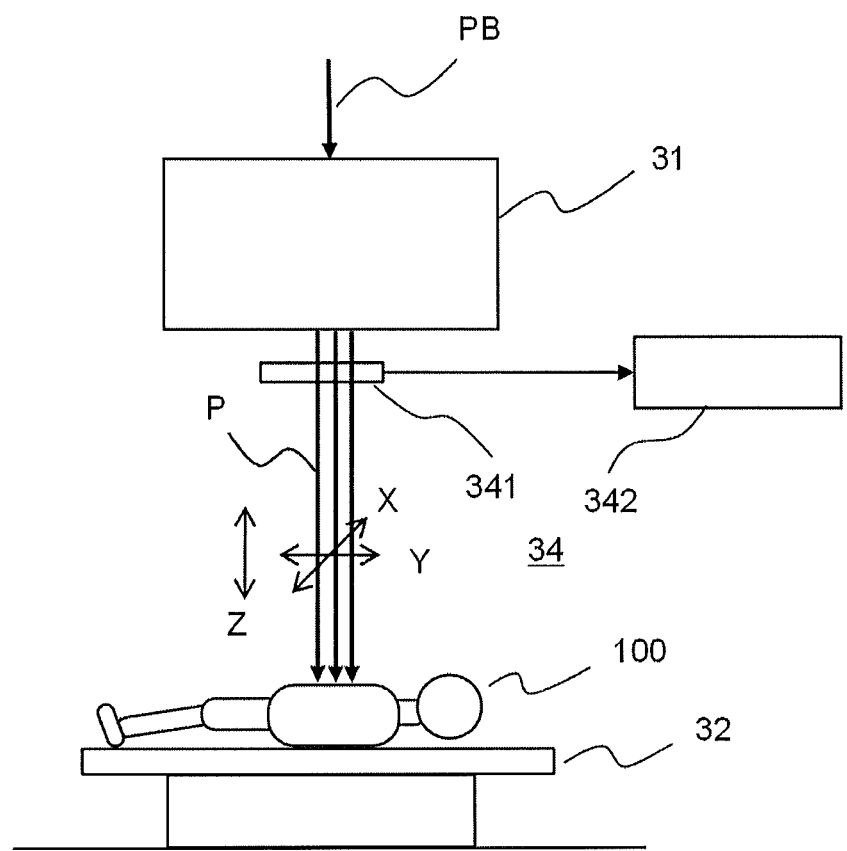
FIG. 3 is a block diagram describing the situation in which the treatment is performed using a particle beam treatment device according to the present invention.
Figure 4:
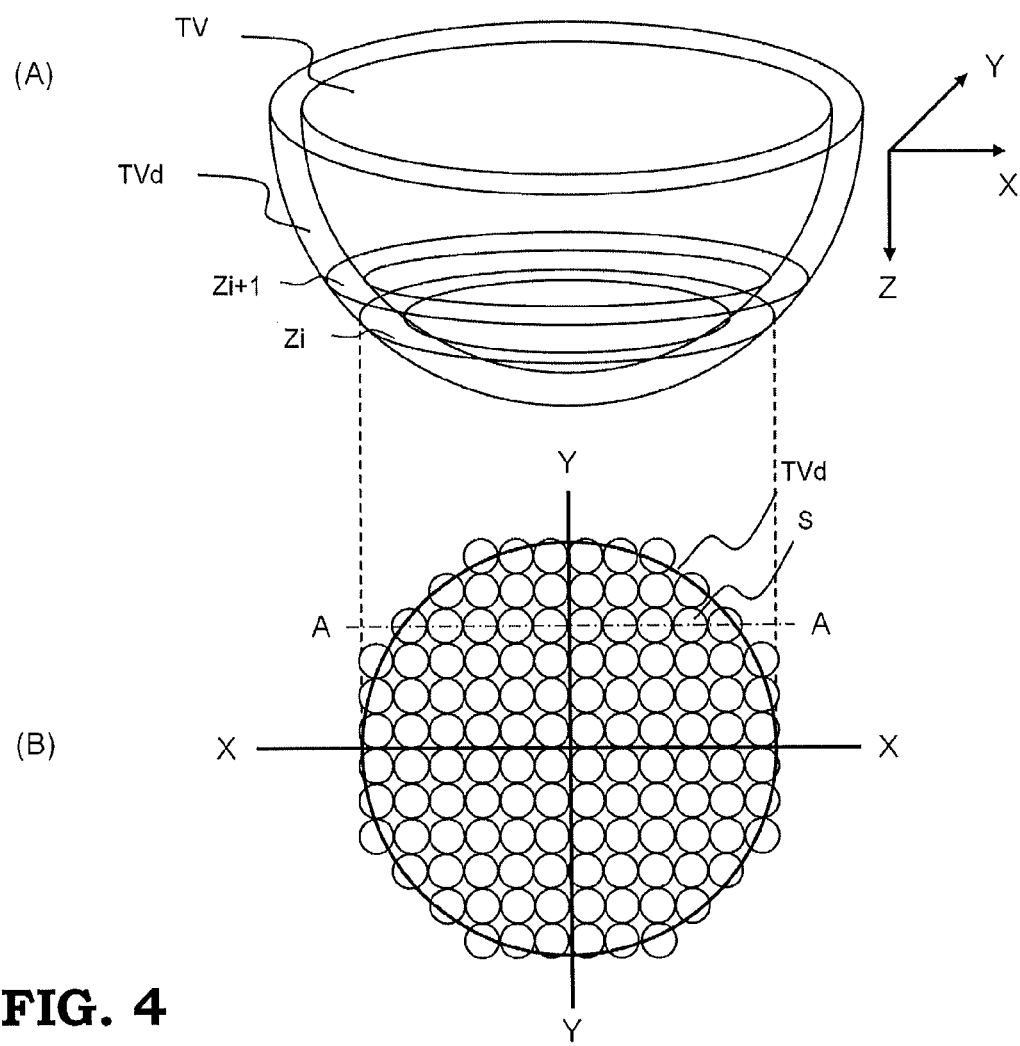
FIG. 4 is a schematic diagram describing the scanning irradiation method.

The particle beam irradiation part 30 constitutes a treatment room. The particle beam irradiation part 30 includes an irradiation nozzle 31, a treatment stand 32 and a positioning device 33. The treatment stand 32 is used for keeping a patient in the state of a dorsal position or a sitting position, and the positioning device 33 is used for confirming the position of an affected organ by an X-ray apparatus or the like. The irradiation nozzle 31 makes the particle beam PB which is transported to the particle beam irradiation part 30 to be a pencil-beam shape so as for a target volume TV of a patient on the treatment stand 32 to be irradiated with the particle beam FIG. 3 shows the state in which a patient 100 who lies down on the treatment stand 32 is irradiated with a particle beam which is emitted from the irradiation nozzle 31 to form a pencil beam P. As shown in FIG. 4, the irradiation nozzle 31 comprises deflection electromagnets (not shown in FIG.) so as to scan an incident pencil beam P laterally (that is, to the X-Y surface which is perpendicular to the beam advancing direction Z). Further, irradiation dose is monitored by a dose monitor 34 which monitors (counts) the dose of the particle beam and the patient 100 is irradiated with the particle beam until the irradiation dose which is counted by the monitor reaches the dose which is set by irradiation dose controller 15. The dose monitor 34 comprises, for example, a dose sensor 341 comprising an ion chamber, etc. and a data processing part 342 which processes the data of count dose which is counted by converting the charge amount which is monitored by the dose sensor 341 to pulses.

Here, a spot scanning irradiation method will be described referring to FIG. 4. FIG. 4(A) is a schematic diagram of a target volume TV, here, a semicircular target volume TV is supposed. A boundary layer TVd is a surface part (boundary part) of this semicircular target volume TV. The dose of the particle beam is given to the whole region of this semicircular target volume, that is, in the depth direction (the z-axis direction), the irradiation volume is spread by changing the particle beam energy, and in the lateral direction (X, Y-axis direction), the irradiation field is spread by scanning the irradiation nozzle 31. In FIG. 4(A), an irradiation layer indicated by Zi is an irradiation layer which is irradiated with a certain particle beam energy Ei, and an irradiation layer indicated by Z i+1 is an irradiation layer which is irradiated with a particle beam energy of Ei+1, wherein the particle beam energy of Ei+1 is smaller than the particle beam energy Ei. Hereinafter, a case in which a layer Zi shown in FIG. 4(A) is irradiated with a certain particle beam energy Ei will be described. FIG. 4(B) is a diagram showing the irradiation method of a pencil beam P of spot scanning method in which the Zi layer is irradiated with the particle beam energy Ei.

In FIG. 4(B), the X-axis in the lateral direction relative to the pencil beam P is indicated by a line X-X, and the Y-axis is indicated by a line Y-Y. The boundary layer TVd of target volume region TV shown in FIG. 4(A) is indicated in FIG.

4(B) by a large circle TVd. Plural irradiation spots which are disposed in the circle TVd and which partially overlap the circle TVd are indicated by a small circle S indicated by a solid line. Irradiation with the pencil beam having a predetermined beam diameter is performed at each spot position until the count value of the dose monitor 34 reaches the target irradiation dose which is set by the irradiation dose controller 15. Spot positions are moved by deflecting the pencil beam with the irradiation nozzle 31. That is, at a spot position is irradiated with the pencil beam until the close reaches the target irradiation dose. After the target irradiation dose is reached, by changing an exciting current of the deflection electromagnets for scanning in the irradiation nozzle 31, an irradiation spot S is moved to an adjacent spot position and the adjacent spot position is irradiated with the particle beam until the dose reaches a target irradiation dose. This operation is repeated, the whole region of Zi layer shown in FIG. 4(A), that is, all spot positions indicated by a small circle shown in FIG. 4(B) are irradiated with the pencil beam having a diameter of the irradiation spot S.

This invention relates to the dose calibration of this target irradiation dose, and provides a method in which irradiation is performed so as to make the biology dose in a target volume (TV) to be the dose which is determined by a treatment plan while controlling the physical irradiation amount by the dose monitor 34 in the scanning irradiation.

Figure 5:
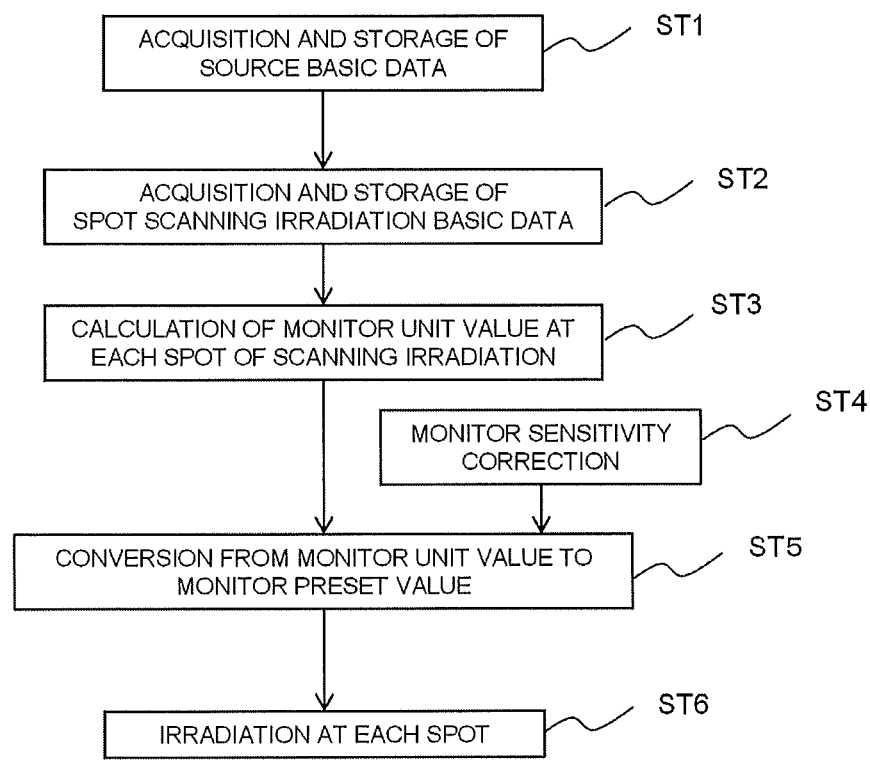
FIG. 5 is a flow chart showing the irradiation dose setting method of a particle beam treatment device according to the present invention.

The outline of a case in which the dose calibration according to this invention is applied to the spot scanning will be shown in FIG. 5. First, as basic data of absorbed dose in a patient's body, using a phantom which imitates the inside of body of the patient, without scanning a pencil beam in the lateral direction, radiation source basic data such as the distribution in the depth direction, that is, the advancing direction of a beam, and the distribution in the lateral direction which is the perpendicular to the advancing direction of a beam is acquired and the acquired data is stored in the treatment planning part 40 (ST1). Further, an example in which water phantom is used will be described. Here, regarding radiation source basic data, a predetermined depth at a part where the depth is shallower than that of Bragg peak, the change of absorbed dose in the depth direction is less, and the dose distribution in the depth is flat is set to be a reference depth, and the data of the reference depth is stored as reference. Next, as described in FIG. 4, the spot scanning irradiation is performed to the water phantom, dose at a predetermined position of the reference depth in the water phantom is acquired, and the acquired dose is stored in the treatment planning part 40 as spot scanning irradiation basic data (ST2). The steps ST1 and ST2 may be performed once for one radiation source.

By using the radiation source data and the spot scanning irradiation basic data, based on biology dose which is the prescription amount which is applied to each patient according to the treatment plan, a monitor unit value at each spot of scanning irradiation in the treatment of the patient (the monitor unit is targeted physical dose, and may be termed as an irradiation dose set value) is calculated (ST3). In the ST3, as the monitor sensitivity may be deteriorated with age, monitor sensitivity correction is periodically implemented, for example, everyday (ST4), and then the conversion from the monitor unit value which is calculated in the step ST3 to a monitor preset value is performed (ST5). By using the preset value which is converted in the step ST5, irradiation is performed for the patient at each spot. Hereinafter, the details of the ST1 to the ST5 will be described in EMBODIMENTS 2 to 5.

Further, here, the spot scanning irradiation is described however, as a method in which beams are not shielded at each spot, a method in which a raster method and a spot method are combined may be performed, and the same effect may be obtained.

Embodiment 2

Figure 6:
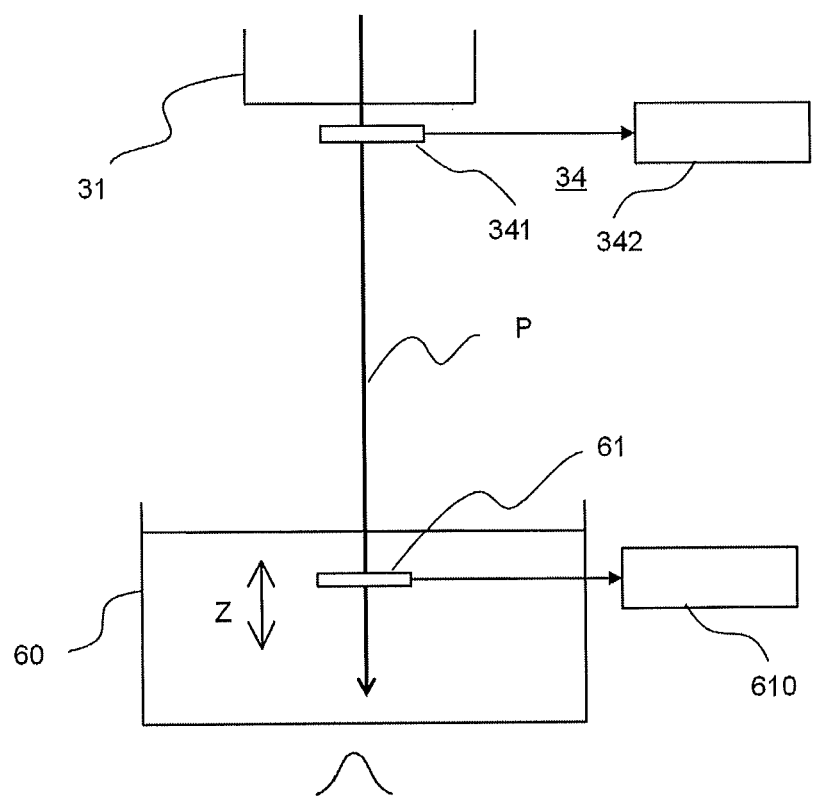
FIG. 6 is a block diagram showing a main part of a device which is used in measuring the absorbed dose distribution in EMBODIMENT 2 of the present invention.
Figure 7:
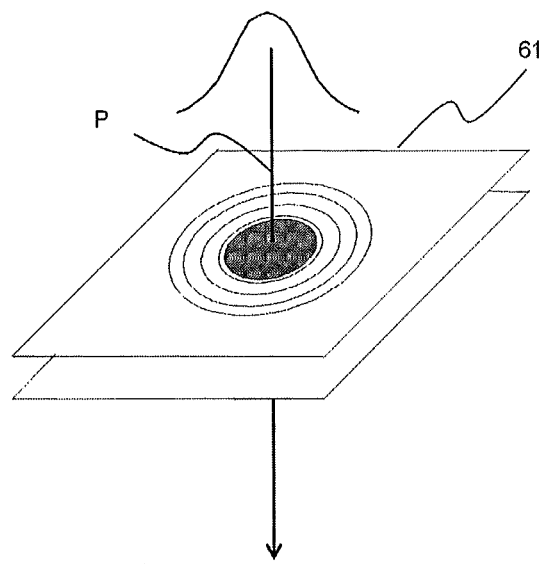
FIG. 7 is a schematic perspective view showing the image of relationship regarding the position between a parallel board-type chamber shown in FIG. 6 and a pencil beam.

FIGS. 6 to 10 are diagrams for describing the details of operation of a particle beam treatment device according to EMBODIMENT 2 of the present invention, that is, acquisition and storing of radiation source basic data in the step ST1 shown in FIG. 5. FIG. 6 is an outline configuration diagram showing a device used in a first step in EMBODIMENT 2. In FIG. 6, the same symbol shows a part which is same as that in FIG. 1 or a corresponding part. A water phantom 60 is irradiated with a pencil beam P having a predetermined beam diameter which is emitted from an irradiation nozzle 31, without scanning the pencil beam P in the X or the Y direction. A dose sensor 341 comprising an ion chamber is arranged between the irradiation nozzle 31 and the water phantom 60. A parallel board-type chamber 61 is provided, to be movable at a part of the water phantom 60 which is irradiated with the pencil beam P, in the advancing direction of the pencil beam P, that is, the Z direction. The charge amount of the parallel board-type chamber 61 is measured by an electrometer 610. FIG. 7 is an enlarged image perspective view showing the relationship between the parallel board-type chamber 61 and the pencil beam P. As shown in FIG. 7, the size of the parallel board-type chamber 61 should be larger than the beam diameter of the pencil beam P having a lateral direction distribution, and the size of the parallel board-type chamber 61 should be large enough for all particle of the pencil beam P can pass through.

Figure 8:
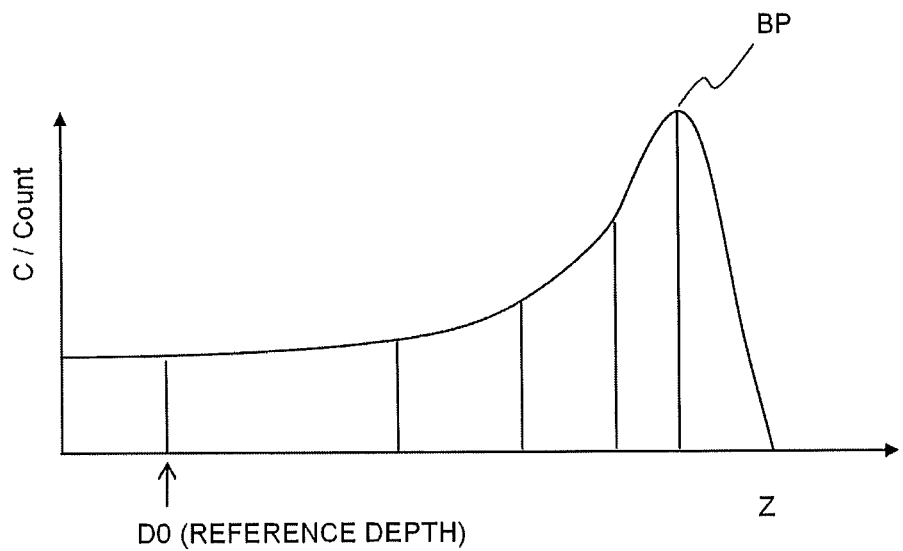
FIG. 8 is a diagram showing one example of data which is acquired by the configuration shown in FIG. 6.

FIG. 8 shows an example of the data which is acquired by the configuration shown in FIG. 6. In this measurement, the data is acquired by moving the parallel board-type chamber 61 to the Z direction, that is, the depth direction of the water phantom 60. Consequently, absorbed dose distribution data in the depth direction PDD (Percentage Depth Dose) can be acquired. A horizontal axis in FIG. 8 is the distance z in the depth direction when the water surface of the water phantom is set to be 0, and a vertical axis is the ratio of the charge amount c which is outputted from the parallel board-type chamber 61 to the outputted count of the dose sensor 341, that is, the output count of the dose monitor 34 at each distance, that is, C/Count. This data is standardized by making a value at the reference depth D0 to be 100%, and the obtained standardized absorbed dose distribution data is inputted to a treatment planning part 40 to be stored. Here, the data is standardized by making a value at the reference depth D0 to be 100% and stored; however, it is not always necessary for the data to be standardized to be stored. As long as a value is stored so as for each value at each distance can be compared each other by using a value at the reference depth as the reference, any storage type may be acceptable.

At plural energy by changing the energy of the pencil beam P, absorbed dose distribution data shown in FIG. 8 is acquired. And the absorbed dose distribution data, which is standardized in which the reference depth at each energy is set to be the reference, is stored in the treatment planning part 40. Regarding the range of the energy, energy is changed from maximum energy to the minimum energy of dose source, and in the range, energy can be used for treatment. Further, changing of the energy can be performed by sending a command from the energy setting controller 14 of the treatment control part 13 shown in FIG. 1 to the accelerator or the particle beam irradiation part 30.

The above-mentioned absorbed dose distribution data PDD in the depth direction may be calculated by simulation using the absorbed dose ratio of energy of particle and a target volume, or phantom, such as water. That is, in advance, PDD is prepared by measurement, or calculation, the PDD may be stored wherein an absorbed dose at the reference depth at a position which is nearer to an incident side of the pencil beam than the position of Bragg peak of PDD which is prepared is the reference, Here, the reference depth will be described. It is preferable that the reference depth is set at a position where the dose distribution in the depth direction is flat as much as possible. In conventional dose calibration, it is general such that the dose calibration is performed by paying attention to the maximum value in PDD, that is, a part of Bragg peak BP where the adsorption is maximum. However, at a position in the vicinity of the Bragg peak BP, as the change of dose distribution is large, when this part is set to be the reference, the error may become large. Then, according to the present invention, the reference depth which is a position as a reference is set to be a position which is shallower than the Bragg peak BP, where the absorbed dose distribution is the state which is almost flat, based on the absorbed dose distribution data acquired at the plural energy. Alternatively, the reference depth is preferably set to be a position where the change of the absorbed dose distribution by distance is less or equal to a predetermined value, that is, preferably, 5%/mm or less, more preferably, 2%/mm or less. In general, as the position is closer to the water surface, the change amount is less. Consequently, when there is no limitation in measurement such as a measurement device including water phantom and a chamber, it is desirable such that the position is at a shallow position such as 5 mm depth or 10 mm depth. Further, regarding high energy, there is less change, however, in low energy, as the Bragg peak BP gets close to the water surface, the change becomes large. Consequently, it is important to determine the reference depth based on the absorbed dose distribution data of low energy. That is, among PDD acquired at plural energy, in the PDD at the lowest energy, the reference depth may be set to a position at which the change of the absorbed dose distribution with distance is a predetermined value or less, for example, 5%/mm or less, more preferably, 2%/mm or less.

In the scanning irradiation, a particle beam to be applied is a pencil beam, during irradiation, there is a distribution which changes greatly in the lateral direction (XY direction), and in the vicinity of Bragg peak BP there is a distribution which also changes greatly in the beam advancing direction (Z direction). As above-mentioned, the absorbed dose distribution in the vicinity of the Bragg peak during irradiation is a distribution which changes greatly in three dimensions. On the other hand, in a position as a reference in the present invention, that is, in the vicinity of the reference depth, as the distribution in the Z direction is flat, the distribution is the absorbed dose distribution in which there is less distribution change in the Z direction, that is, the distribution which is changed only in two dimensions. As above mentioned, the effect of the absorbed dose distribution can be decreased by one dimension, and this is an important point of this invention.

Figure 9:
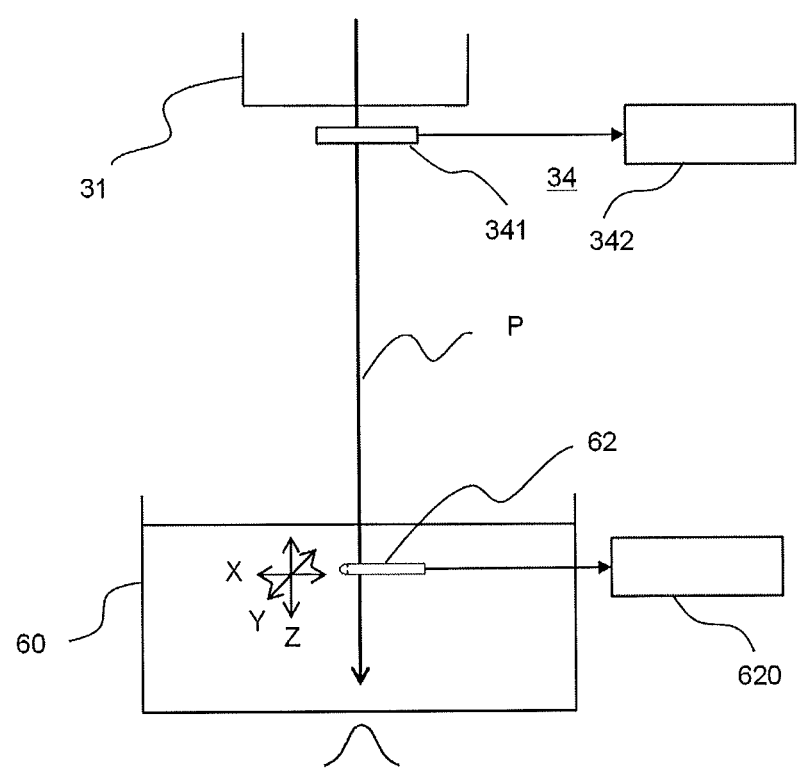
FIG. 9 is a block diagram showing a main part of a device which is used in measuring the dose distribution in lateral direction of a pencil beam in EMBODIMENT 2 of the present invention.
Figure 10:
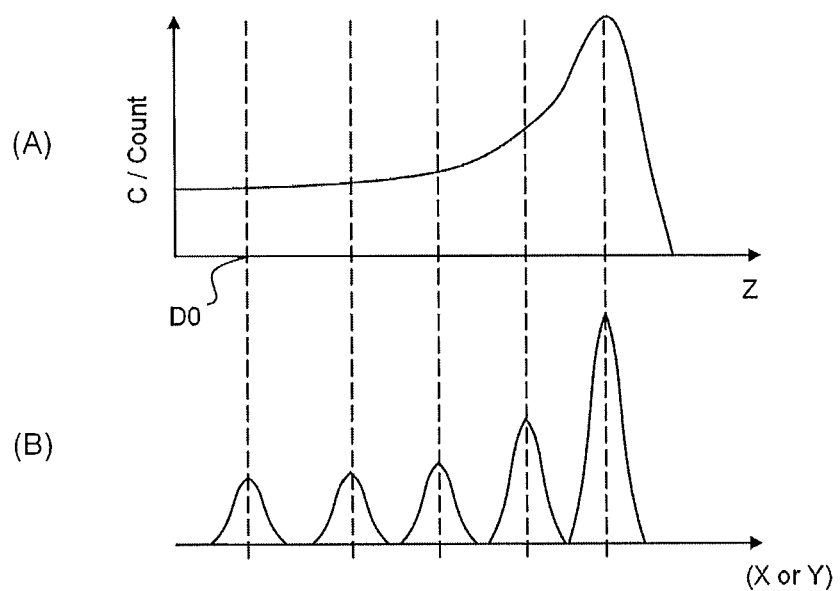
FIG. 10 is a diagram showing one example of data which is acquired by the configuration shown in FIG. 9.

Next, as a second stage of EMBODIMENT 2, among the basic data of the dose source, lateral direction distribution (OCR: Off Center Ratio) of absorbed dose by a pencil beam P which does not scan in the X direction or the Y direction is acquired. FIG. 9 shows the configuration of a device which acquires the lateral direction distribution. In FIG. 9, the same symbol as that of FIG. 6 indicates the same part. The different point regarding the configuration between FIG. 6 and FIG. 9 is such that in FIG. 6, a sensor in the water phantom is the parallel board-type chamber 61, however, in FIG. 9, the sensor is a thimble chamber 62. The charge amount of the thimble chamber 62 is measured by an electrometer 620. The parallel board-type chamber 61 has a shape through which all pencil beams PB can pass, however, a size of the thimble chamber 62 is smaller than that of the pencil beam. For example, a beam diameter of the pencil beam is σ5 mm; a measuring area of the thimble chamber 62 has a radius of 1 mm and a length of 5 mm. By moving this thimble chamber 62 in the X-Y direction at a position of a certain depth Z, the XY two-dimensional dose distribution can be acquired. On this occasion, by measuring the dose so as to move the chamber in the direction of a radius of 1 mm, the resolution can be improved. This measurement at the reference depth, a Bragg peak position and other plural depth positions is performed. FIG. 10 shows the image of acquired date. FIG. 10(A) shows the absorbed dose distribution in the depth direction in the same way as that of FIG. 8. FIG. 10(B) shows the lateral direction distribution (X or Y) in which dose is acquired at each depth (Z). This data is also acquired by changing the energy; the data of lateral direction distribution at each depth at each energy is stored as one dose source basic data in the treatment planning part 40. In this regard, in a case where the measured result is similar enough to the gauss distribution when the measured result is compared to the gauss distribution, not the measured result but the ideal gauss distribution may be stored. In the same way, the distribution in which two or three ideal gauss distributions are combined may be used. This distribution data is not effective to an absolute value in the dose calibration in the present invention, but is used for calculation of dose distribution which is performed in a treatment planning device; therefore, this distribution data has little influence. By the above-mentioned, acquisition the radiation source basic data in the step ST1 and storing the data in the treatment planning part 40 is completed.

Embodiment 3

Figure 11:
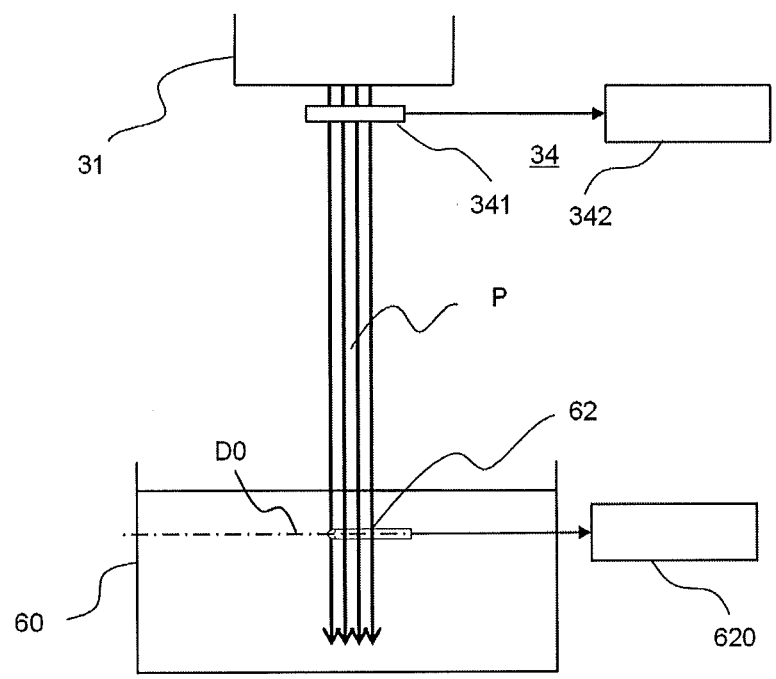
FIG. 11 is a block diagram showing a main mart of a device which is used in EMBODIMENT 3 of the present invention.
Figures 12, 13:
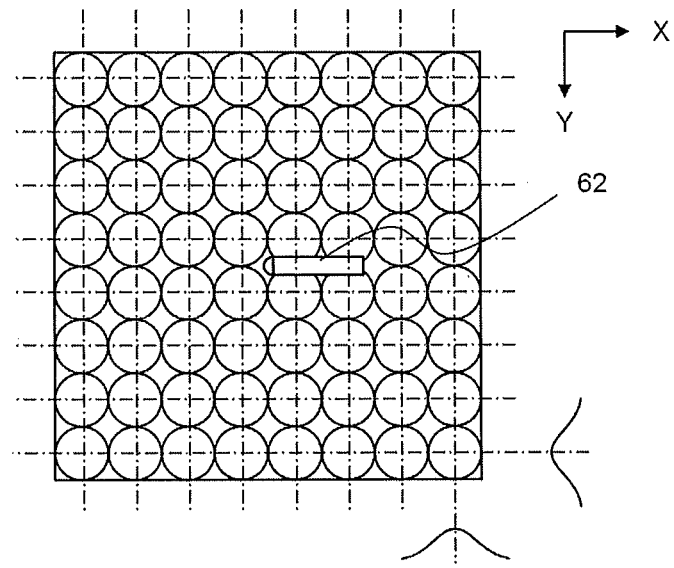
FIG. 12 is a diagram for explaining the outline of measurement in EMBODIMENT 3 of the present invention.
FIG. 13 is a table showing one example of energy correction coefficient which is calculated in EMBODIMENT 3 of the present invention.

FIGS. 11 to 13 are diagrams for describing the details of operation of a particle beam treatment device in EMBODIMENT 3 of the present invention, that is, acquisition and storing of basic data of the spot scanning irradiation which is the operation in the step ST2 shown in FIG. 5. FIG. 11 is an outline configuration diagram showing a main part of a particle beam treatment device used in EMBODIMENT 3. In the step ST2, a pencil beam P is scanned, and the absorbed dose data is acquired by a thimble chamber 62 which is set at a predetermined position at the reference depth D0. FIG. 12 shows the image of the spot scanning irradiation which is performed on a surface of the reference depth in this measurement. When this measurement is performed, the condition to make the dose distribution at a part in the reference depth (plato), which is applied by the irradiation for one slice, that is, by irradiation with a certain energy, uniform is obtained. On this occasion, this measurement is performed at each energy used in a treatment. When the energy is different, the spot diameter in a water phantom is different. Therefore, the pitch which makes the distribution uniform is different and the energy which passes through the dose monitor 341 is different. Consequently, the measurement result (count value) to be obtained is different. Further, the reference size and pitch of the spot is predetermined at each energy, and the uniform dose distribution is formed by using the reference size and pitch. On this occasion, it is not necessary to form the uniform dose distribution with respect to the whole irradiation field, and the condition, such that the field size is much larger than that of the thimble chamber 62 and the measurement error due to the position error of the thimble chamber 62 is not caused, is only required. In order to satisfy the above-mentioned condition, for example, the scanning irradiation which is performed at an area having 10 cm×10 cm square is assumed. That is, the pencil beam P is scanned for irradiation so as to make an area which is indicated by the outer square shown in FIG. 12 to be the area having 10 cm×10 cm square. A circle shown in FIG. 12 shows each spot of the pencil beam. A position of the thimble chamber 62 is set to be the center of the area having 10 cm×10 cm square.

Regarding the irradiation dose at each spot, irradiation is performed until the counted value by a dose monitor 34 reaches a predetermined value (preset value). That is, at each spot, the same value of preset value is set, and irradiation is performed in a range which is shown in FIG. 12. The value which is measured by the thimble chamber 62 in a case where all spots are irradiated, that is, the dose value Gy is measured. On this occasion, even when the preset value is same, there is a case in which the value which is counted by the dose monitor 34 in a case where irradiation is actually performed at each spot is slightly different. This is because the error with respect to an instruction value which is the preset value may be caused due to the variation of the interrupting time of a beam at each spot after finishing the irradiation. Consequently, the actual count value by the dose monitor at each spot is obtained, and the average amount "Count" of the count value is calculated. Based on the dose value Gy and the average count value "Count", the monitor correction coefficient Gy/Count at the reference depth is calculated. The above-mentioned calculation is performed at each energy which is same as that acquired by the step ST1, and the data of Gy/Count at the reference depth at each energy is acquired. Here, among the energy which is used for measurement, the reference energy is set, and the ratio of Gy/Count at each energy to Gy/Count at the reference energy is obtained. This ratio is stored in a treatment planning part 40 as the energy correction coefficient of each energy. The reference energy may be the maximum energy. An example of energy correction coefficient which is stored in the treatment planning part 40 is shown in a table in FIG. 13.

Embodiment 4

By performing the step ST1 which is described in EMBODIMENT 2 and the step ST2 which is described in EMBODIMENT 3 once for each radiation source, PDD data which is standardized for each energy and the energy correction coefficient at each energy in a spot scanning irradiation are stored in a treatment planning part 40. In EMBODIMENT 4, a method in which the dose which is applied to an affected part of a patient is converted to a monitor unit value (MU) by using the PDD data and the energy correction coefficient which is stored in the treatment planning part 40, that is, a step ST3 will be described. This monitor unit value is outputted from the treatment planning part 40 to an irradiation dose controller 15.

The dose which is applied to an affected part of a patient is given by a biology dose for each patient according to a treatment plan. In the treatment planning part 40, the biology dose which is given by the treatment plan is stored as data, based on this biology dose, the physical dose at each spot is converted so as to calculate a monitor unit value. The dose at each spot is designated corresponding to the weight of each spot to the entire affected part, and the dose at each spot is calculated by distributing a monitor unit value with the weight at each spot. Here, the weight at each spot is set so as for the total of weight at all spots to be one.

Figure 14:
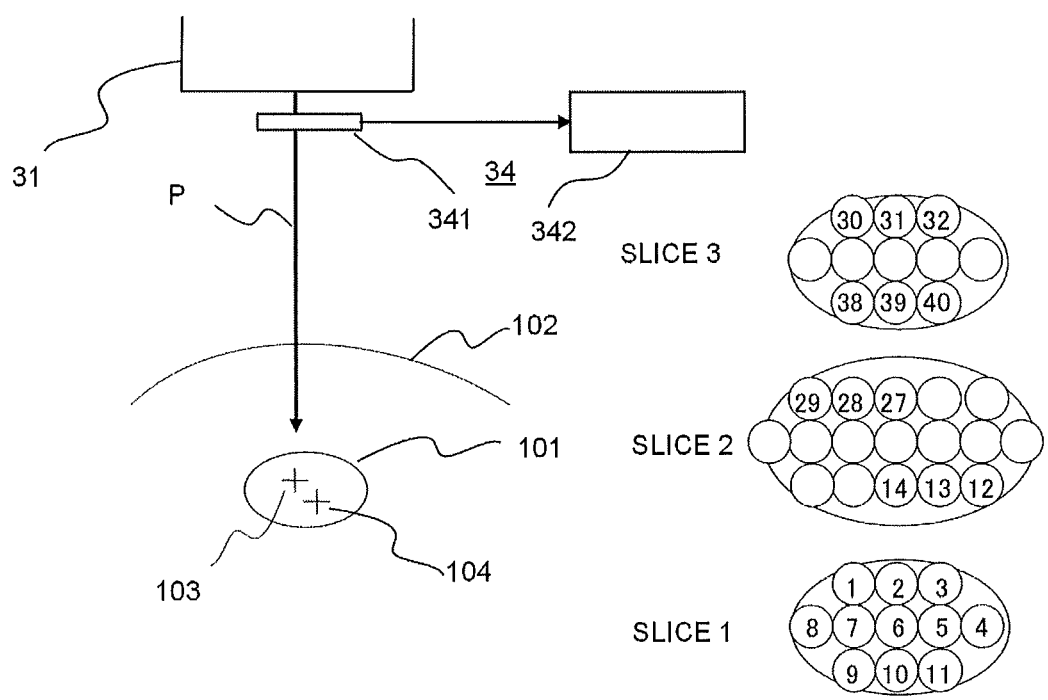
FIG. 14 is a diagram showing the image when a target volume is irradiated with a particle beam according to the scanning irradiation method by a particle beam treatment device of the present invention.

FIG. 14 shows the image when an affected part is irradiated with a particle beam. A pencil beam P enters from the surface of a body of a patient to inside of the body, and an affected part 101 is irradiated with the pencil beam P. In the treatment plan, inside the affected part 101, an isocenter 103 and a beam dose specification point 104 are set. The isocenter 103 is a geometric point which is used for positioning of patient, and the beam dose specification point 104 is a point for giving the biology dose for applying to the affected part. When the shape of an affected part is a shape which has the closed surface at each section, such as a spherical form, it is often the case that the isocenter 103 coincides with the beam dose specification point 104. However, in a case where an affected area is a hollow shape, the isocenter 103 is not inside the affected part, therefore, the point is not used as a beam dose specification point. The biology dose at the beam dose specification point 104 is designated as the unit GyE.

For each energy, an effected part in a depth which is the Bragg peak of the energy is an irradiation layer (slice), and when the energy is changed, the slice is changed. During the irradiation for treatment, for each slice, when a value of a dose monitor 34 reaches a monitor preset value corresponding to a monitor unit value (MU) which is designated at each spot, a pencil beam P is moved laterally so as to perform the irradiation at next spot. Accordingly, the irradiation is performed sequentially. When the irradiation of one slice is completed, the energy of the particle beam is changed so as to perform irradiation at next slice. The right side of FIG. 14 shows the image in which irradiation is performed in descending order of energy by changing the energy. A slice which is irradiated with a particle beam having the highest energy is slice 1, a spot 1 to a spot 11 are irradiated, when the irradiation for entire of the slice 1 is completed, the energy is slightly decreased and then a slice 2 is irradiated. In a slice 2, spots 12 to 29 are irradiated, then, the energy is further decreased and spots 30 to 40 in a slice 3 are irradiated. As above-mentioned, in a scanning irradiation, a plurality of spots are irradiated for each slice, however regarding the designation of monitor unit value MU for each spot, the monitor unit value MU itself may be designated, alternatively, the designation may be performed by the weight with respect to the total monitor unit value MU.

MU and weight at each spot are calculated by the following step. MU at each spot is calculated based on the biology dose at each spot position, the energy correction coefficient and PDD which is stored in the treatment planning part 40. Here, a spot position is a position of Bragg peak, that is, the position of the peak of PDD. Therefore, at each energy, Dp/Do, which is the ratio of the absorbed dose Dp at the peak position of PDD to the absorbed dose Do at the reference depth is obtained and the obtained value is the depth coefficient. Based on the above-mentioned values, Mu at each spot is calculated by equation (1).

$$\text{MU OF EACH SPOT} = \frac{\text{BIOLOGY DOSE } (cGyE) \text{ AT SPOT POSITION}}{RBE \times \text{DEPTH COEFFICIENT} \times \text{ENERGY CORRECTION COEFFICIENT}} \quad (1)$$

Here, RBE is the biological effect ratio which is determined by a kind of particle beams. Here, this RBE includes the irradiation field coefficient in the spot scanning irradiation (since only the dose of spot which is adjacent is not contributed because of the spread of the gauss distribution, in a case where the area to be irradiated is small, even the same dose is applied, the absorbed dose becomes small, therefore, it is necessary such that correction coefficient is introduced.).

When MUs of all spots are calculated, the weight of each spot can be calculated by equation (2). This weight is not the weight of dose at a spot but the weight which shows the distribution of the monitor unit value MU.

$$\text{WEIGHT OF EACH SPOT} = \frac{\text{MU OF EACH SPOT}}{\text{MU OF TOTAL SPOT}} \quad (2)$$

According to the above-mentioned procedure, the calculated monitor unit value MU is designated by the treatment planning part 40. This monitor unit value MU is designated by the condition such that the dose at the reference depth is made to be 1 cGy (centigray, 0.01Gy) by applying the irradiation of 1 MU with the reference energy and the reference spot pitch.

Embodiment 5

The sensitivity of a dose monitor 34 is deteriorated with age, therefore, the sensitivity correction is necessary. EMBODIMENT 5 regards to the sensitivity correction of the dose monitor 34, that is, the steps ST4 and ST5. The sensitivity correction should perform periodically, for example, every day. First, only at the reference energy, data of the monitor correction coefficient Gy/Count at the reference depth; Gy/Count in the step ST2 which is described in EMBODIMENT 3 is acquired. Next, the monitor correction coefficient is calculated by obtaining the ratio of 0.01 Gy/MU, which is the reference of the monitor unit MU, and the monitor correction constant. Further, in general, a thimble chamber is used by assuring the absolute sensitivity by performing calibration, here, the thimble chamber whose absolute sensitivity is assured is used.

$$\text{MONITOR CORRECTION COEFFICIENT} = \frac{\text{MONITOR CORRECTION COEFFICIENT } (Gy/Count)}{0.01 \ (Gy/MU)} \quad (3)$$

Each spot preset, which is a target value of irradiation dose set value at each spot in actually performing irradiation for treatment can be obtained by dividing a monitor unit value (MU value) at each spot which is designated by a treatment planning part 40 by the monitor correction coefficient which is calculated by the equation (3) and by converting by the following equation (4).

$$\text{PRESET AT EACH SPOT} = \frac{\text{MU OF EACH SPOT}}{\text{MONITOR CORRECTION COEFFICIENT } (Gy/\text{Count})} \quad (4)$$

As above-mentioned procedure, the irradiation dose, which is applied to an affected part as biology dose in a treatment plan, can be converted to the physical dose, which can be controlled in actual treatment, without performing complicated procedures and accurately. Then, preset of each spot which is obtained by the equation (4) is outputted from the treatment planning part 40 to the irradiation dose controller 15 as an irradiation dose set value. In applying irradiation to each spot of an affected part (ST6), when a count value of the dose monitor 34 reaches the preset of each spot, the irradiation dose controller 15 performs the control to complete the irradiation at the spot.

Embodiment 6

1 MU is given as a count value of a dose monitor which makes the dose at the reference depth to be 1 cGy, in a case where a pitch is the reference pitch. Consequently, when a pitch of a spot is not the reference pitch, it is necessary to correct a MU value. EMBODIMENT 6 regards to a method for calculating a MU value in a case where a pitch is not the reference pitch.

Figure 15:
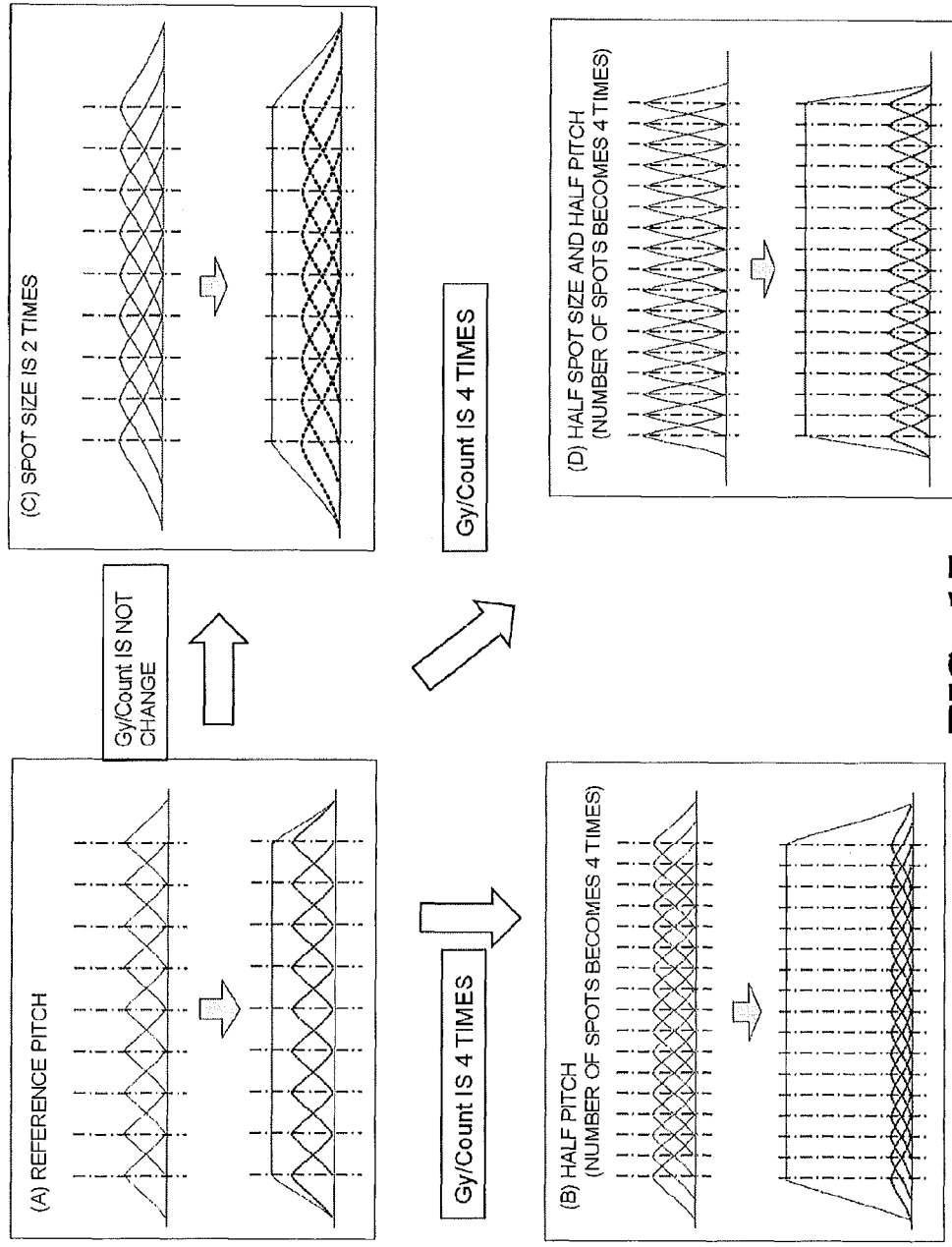
FIG. 15 is a diagram for explaining the irradiation dose setting method of a particle beam treatment device in EMBODIMENT 6 of the present invention.

FIG. 15 shows the image in a case where a pitch is different. FIG. 15(A) shows the image of dose distribution in scanning irradiation in a case where pith is the reference pitch and a size of a spot is the reference spot size. FIG. 15(B) shows the image of dose distribution in a case where the spot size is the reference spot size and the pitch is changed to be the half of the reference pitch. Since the pitch is changed to be the half of the reference pitch, in a case where the scanning irradiation is performed at an area having 10 cm×10 cm square, which is the same area which is described in EMBODIMENT 3, the number of spot to be irradiated becomes four times, the total dose for irradiation becomes four times. Consequently, Gy/Count becomes four times of the Gy/Count which was obtained in a case where a pitch is the reference pitch. Consequently, in a case where a pitch is the half of the reference pitch in actual treatment, it is necessary to make the MU value to be one fourth.

FIG. 15(C) shows the image of the dose distribution in a case where a spot size is twice as that of the reference size and the pitch of a spot is the reference pitch. In this case, the number of spot is the same; therefore, GY/Count is the same as that in a case where a spot size is the reference size. Consequently, when only the spot size in actual treatment is different from that of the reference size, it is not necessary to correct a MU value in case where the pitch is the reference pitch, FIG. 15(D) shows the image of the dose distribution in a case where the spot size and the pitch is the half of that of the reference size. In this case, in the same way as that shown in FIG. 15(B), the number of spot becomes four times and the total doze to be irradiated becomes four times. Consequently, Gy/Count becomes four times as Gy/Count which is obtained when the pitch is the reference pitch. Consequently, in a case where the pitch in actual treatment is the half of the reference pitch, it is necessary to make the MU value to be one fourth.

As above mentioned, in a case where the scanning irradiation is performed using a spot whose pitch is not the reference spot pitch, in the treatment planning part 40, as above mentioned, it is necessary to correct a MU value by dividing the ratio of the spot number, corresponding to the ratio of the number of spot with respect to the irradiation of the reference pitch. However, it is necessary for the pitch not to be too large with respect a beam diameter of a pencil beam P so as to make the dose distribution to be uniform in an irradiation field.

Embodiment 7

EMBODIMENTS 3 to 6 describe a case in which an irradiation spot is moved stepwise for performing irradiation, that is, so-called spot scanning irradiation is applied to the present invention. In addition to the spot scanning irradiation, other type of irradiation such as so-called raster scanning in which a pencil beam is moved continuously can be applied to the present invention. EMBODIMENT 7 describes a case in which the raster scanning irradiation is applied to the present invention.

Figure 16:
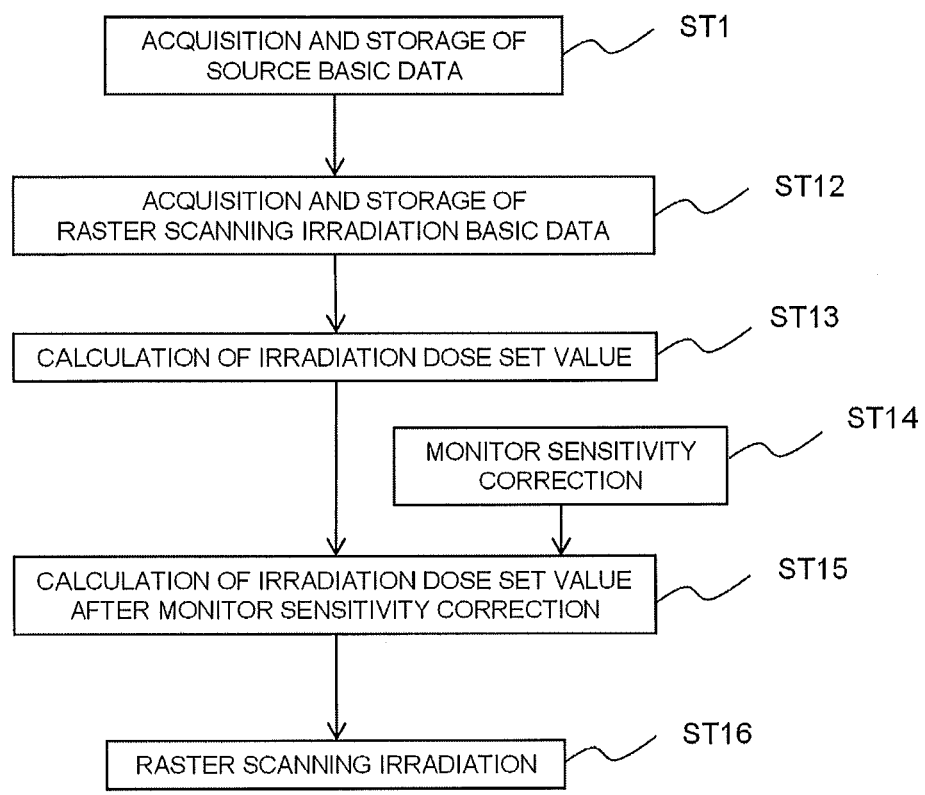
FIG. 16 is flow sheet showing the irradiation dose setting method of a particle beam treatment device in EMBODIMENT 7 of the present invention.

FIG. 16 shows the outline of a case in which the dose calibration according to the present invention is applied to the raster scanning irradiation. First, as basic data of absorbed dose in a patient's body, using a phantom which imitates the inside of patient's body, without scanning the pencil beam laterally, radiation source basic data such as the distribution of the depth direction, that is, the advancing direction and the lateral direction distribution which is the perpendicular direction to the beam advancing direction is acquired and the acquired data is stored in the treatment planning part 40 (ST1). Here, regarding radiation source basic data, a predetermined depth at a part where the depth in the depth direction is shallower than that of Bragg peak, the change of absorbed dose in the depth direction is less, dose distribution in the depth is flat is set to be a reference depth, and the data of the reference depth is stored as reference. In this step ST1, the data is acquired without scanning the pencil beam laterally, and is the completely same as that is described in details in EMBODIMENT 2.

Figure 17:
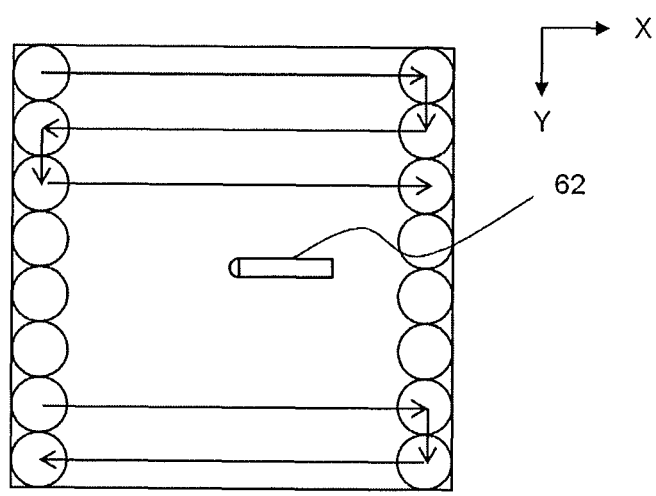
FIG. 17 is a diagram for explaining the outline of measurement in EMBODIMENT 7 of the present invention.
Figure 18:
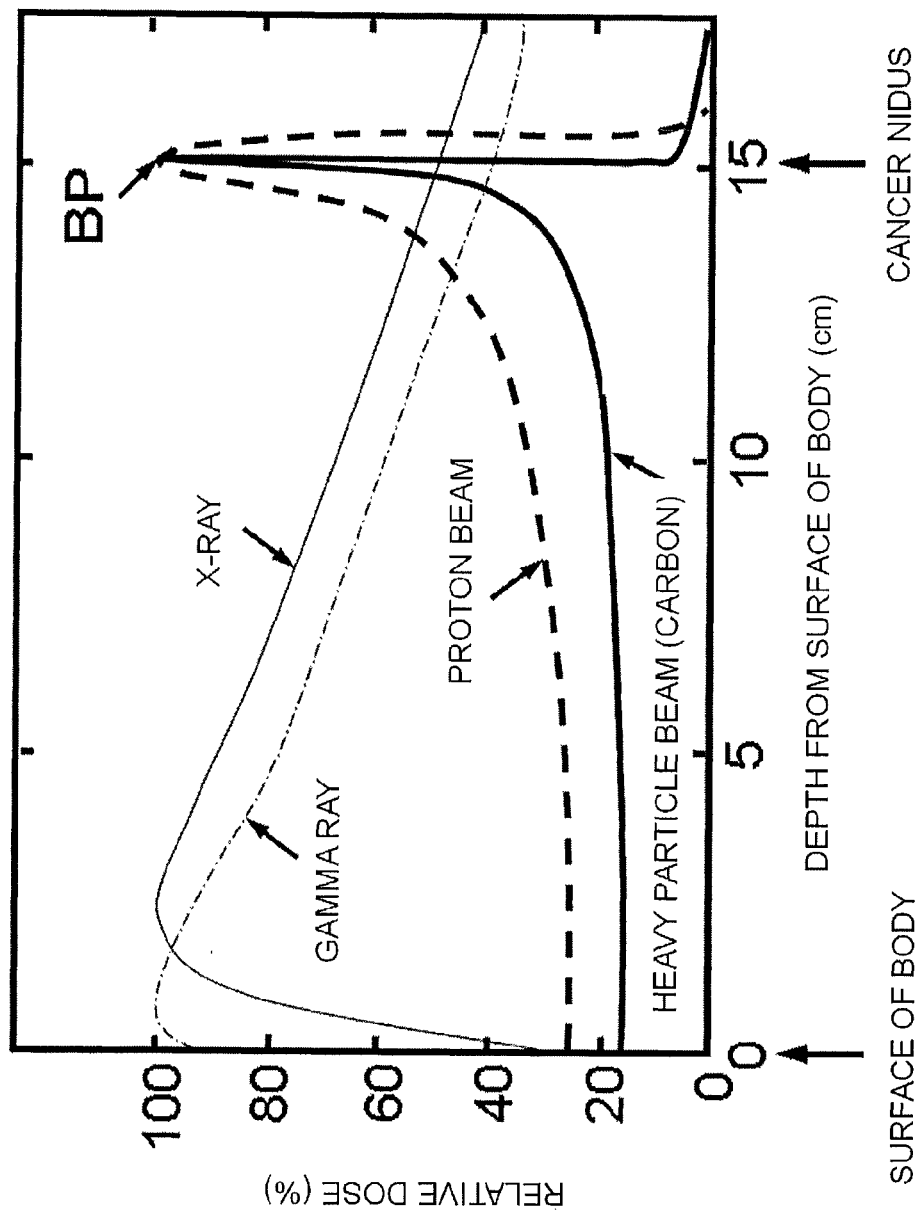
FIG. 18 is a diagram showing the dose distribution of radiation beam inside of a body in a case where various kinds of radiation beams are applied to the human body.

Next, as shown in FIG. 17, the raster scanning irradiation for one slice is performed to water phantom, the dose at a predetermined position in the reference depth in the water phantom is acquired, and the acquired dose is stored in the treatment planning part 40 as raster scanning irradiation basic data (ST12). The steps ST1 and ST12 may be performed once for one radiation source.

By using the radiation source basic data and the raster scanning irradiation basic data, based on biology dose which is the prescription dose which is applied to each patient according to the treatment plan, an irradiation dose set value in the raster scanning irradiation in treatment of the patient is calculated (ST13). In the ST13, as the monitor sensitivity may be deteriorated with age, monitor sensitivity correction is periodically implemented, for example, everyday (ST14), the irradiation dose set value which is calculated in the step ST13 is corrected so as to calculate an irradiation dose set value which is obtained after the monitor sensitivity is corrected (ST15). By using the irradiation dose set value which is calculated in the step ST15, raster scanning irradiation is applied to a patient (ST16). Hereinafter, the details of steps ST12 to ST15 will be described.

The raster scanning irradiation basic data in the step ST12 will be acquired as following. The configuration of the main part of a particle beam irradiation device to be used is same as that shown in FIG. 11 in EMBODIMENT 3. FIG. 17 shows the outline of acquisition of raster scanning irradiation basic data. In FIG. 17, a circle indicates an irradiation spot of a pencil beam, and this irradiation spot is moved continuously in the direction shown by an arrow. In FIG. 17, an irradiation is started to apply from an upper left position, the irradiation spot is moved to the right position (X direction), at the right edge of an irradiation region, the irradiation spot is moved to a lower position (Y direction) by the distance corresponding to one spot (one pitch length), and then is moved to the left direction. This operation is repeated, and when the irradiation spot is moved to a lower left position, the irradiation is completed. In a case where an irradiation dose is insufficient, the above-mentioned operation may be repeated for plural times.

In the step ST12, a pencil beam P is scanned continuously (raster scanning) as above-mentioned, and absorbed dose data is acquired by a thimble chamber 62 which is provided at a predetermined position in the reference depth D0 in the same way as shown in FIG. 11. When this measurement is performed, the condition to make the dose distribution at the reference depth uniform by applying the irradiation for one slice, that is, irradiation with certain energy is obtained. On this occasion, the energy to be used is changed for each treatment. When the energy is different, the spot diameter in a water phantom is different, depending on energy, the scanning speed in the X-direction and the pitch in the Y direction to make the distribution uniform is different and the energy which passes through a dose sensor 341 is different. Consequently, the measured result (count value) to be obtained is different. Further, regarding the size of a spot, the pitch in the Y direction and the scanning direction in the X direction, the reference is determined so as to form the uniform dose distribution by using the reference. On this occasion, it is not necessary to form the uniform dose distribution with respect to the whole irradiation field, the condition such that the size is larger than that of the thimble chamber 62, and the measurement error due to the position error of the thimble chamber 62 is not caused is only required. In order to satisfy the above-mentioned condition, for example, the scanning irradiation which is performed at an area having 10 cm×10 cm square is assumed. That is, a pencil beam P is scanned for irradiation so as to make an area which is indicated by the outer square shown in FIG. 17 to be the area having 10 cm×10 cm square. A circle shown in FIG. 17 shows each spot of a pencil beam. A position of the thimble chamber 62 is set to be the center of the area having 10 cm×10 cm square.

In a case where the raster scanning irradiation is performed, the dose which is applied to the irradiation field is proportional to the current value which is obtained by measuring the dose of pencil beam per unit time by a dose monitor, or proportional to the value which is obtained by dividing the beam current which is emitted from an accelerator by the X direction scanning speed (mm/sec), that is, C/mm. Consequently, the scanning speed is determined by the dose value of a pencil beam per unit time, and then, the above-mentioned area having 10 cm×10 cm square is irradiated with the raster scanning. When the whole area is irradiated, the value of the thimble chamber 62, that is, the dose value Gy is measured. On the other hand, the average value of the C/mm is obtained by the count value of the dose monitor 34 per unit time and the scanning speed in actual irradiation. Then, based on the dose value Gy and the average value of the C/mm, the monitor calibration at the reference depth Gy/(C/mm) is calculated. The above-mentioned measurement is performed at each energy which is the same as that of PDD data which is acquired in the step ST1, the data of Gy/(C/mm) at the reference depth at each energy is acquired. Here, among the energy which is used for measurement, the reference energy is set, the ratio of Gy/(C/mm) at each energy and Gy/(C/mm) at the reference energy is obtained. The obtained ratio is stored as the energy correction coefficient in the treatment planning part 40 together with the Gy/(C/mm). The reference energy may be the maximum energy, for example.

The above-mentioned steps ST1 and ST12 are performed once for a dose source so as to store the PDD data which is standardized of each energy, the energy correction coefficient of each energy in the raster scanning irradiation in the treatment planning part 40. Next, a method for converting to the irradiation dose set value in applying the irradiation to an affected part of a patient by using the PDD data and the energy correction coefficient which is stored in the treatment planning part 40. This irradiation dose set value is outputted from the treatment planning part 40 to the irradiation dose controller 15.

In a case where the raster scanning irradiation is performed, an affected area in the depth which is the Bragg peak of this energy becomes an irradiation layer (slice) of each energy, and when the energy is changed, the slice is changed. In irradiation for treatment, for each slice and irradiation position, the irradiation is performed by moving a pencil beam laterally so as to make a value which is calculated based on a value of the dose monitor 34 and the scanning speed of a pencil beam to be an irradiation dose set value C/mm. When the irradiation of one slice is completed, the energy of a particle beam is changed, and then irradiation is performed for next slice. In this way, in the raster scanning irradiation, a pencil beam is moved continuously so as to perform irradiation for each slice, the dose set in this occasion is set by the irradiation dose controller 15 as an irradiation dose set value. Here, in order to control the irradiation dose to be the irradiation dose set value, for example, the number of particle beam which is outputted from an accelerator or the scanning speed of the pencil beam may be controlled. Further, in a case of the raster scanning irradiation, it is preferable that a cyclotron is used as an accelerator.

The irradiation dose set value C/mm is calculated based on the biology dose GyE, biological effect ratio of a particle beam RBE and an energy correction coefficient, PDD, and Gy/(C/mm), which are stored in the treatment planning part 40. Here, an irradiation position is a position of Bragg peak, that is, the peak position of PDD. At each energy, the ratio of the absorbed dose Dp at the peak position of PDD to the absorbed dose D0 at the reference depth, Dp/D0 is obtained so as to be the depth coefficient, and the irradiation dose set value is calculated based on RBE and Gy/(C/mm). Based on the above-mentioned each value, the irradiation dose set value C/mm at each irradiation position in the irradiation volume TV is calculated according to next equation (5).

$$\text{IRRADIATION DOSE SET VALUE C/mm AT EACH IRRADIATION POSITION} = \frac{\text{BIOLOGY DOSE } (GyE) \text{ AT EACH IRRADIATION POSITION}}{RBE \times \text{DEPTH COEFFICIENT} \times \text{ENERGY CORRECTION COEFFICIENT} \times (Gy/(C/mm))} \quad (5)$$

As the sensitivity of the dose monitor 34 is deteriorated with age, it is necessary to perform the sensitivity correction. The sensitivity correction of the dose monitor is periodically implemented, for example, everyday (ST14). First, regarding the data of monitor calibration at the reference depth Gy/(C/mm) in the step ST12, only the data regarding the reference energy is acquired. Next, the monitor correction coefficient is calculated by using the monitor calibration constant Gy0/(C/mm) at the reference depth regarding this reference energy (ST14). Based on this monitor correction coefficient, the irradiation dose set value C/mm which is calculated in the step ST13 is corrected so as to determine the irradiation dose set value which is obtained after the monitor sensitivity correction (ST15). By using this irradiation dose set value which is obtained after the monitor sensitivity correction, the raster scanning irradiation is applied to a patient (ST16).

As above-mentioned, the irradiation dose which is applied to an affected part as biology dose in a treatment plan can be converted to physical dose of dose monitor which can be controlled in actual treatment or the scanning speed of a pencil beam without performing complicated procedures and with accuracy.

DESCRIPTION OF REFERENCE NUMERALS AND SIGNS

| | |
|---|---|
| 1, 2: | treatment room |
| 10: | particle beam generation part |
| 11: | injector |
| 12: | accelerator |
| 13: | treatment control part |
| 14: | energy setting controller |
| 15: | irradiation dose controller 15 |
| 20: | particle beam transport part |
| 30, 30A, 30B: | particle beam irradiation part |
| 31: | irradiation nozzle |
| 32: | treatment stand |
| 33: | positioning device |
| 34: | dose monitor |
| 341: | dose sensor |
| 342: | data processing part |
| 40: | treatment planning part |
| 60: | water phantom |
| 61: | parallel board-type chamber |
| 62: | thimble chamber |
| 100: | patient |
| P: | pencil beam |
| PB: | particle beam |

The invention claimed is:

1. A particle beam treatment device comprising
an irradiation nozzle for radiating a particle beam as a pencil beam to a target volume so as to form a spot of the particle beam which is the maximum adsorption region at a position in the depth direction of the target volume which is determined by the energy of the particle beam, and for radiating a particle beam to the target volume by moving the pencil beam in the lateral direction which is perpendicular to the advancing direction so as to move the position of the spot in the lateral direction;
a dose monitor which measures the dose of the particle beam which is emitted from the irradiation nozzle;
a treatment planning part which sets an irradiation dose set value which is applied to the target volume;
a treatment control part having an energy setting controller which sets the energy of the particle beam, a beam scanning controller which controls the irradiation nozzle, and an irradiation dose controller which controls an irradiation dose which is applied to the target volume based on a measurement value of the dose monitor and the irradiation dose set value which is set by the treatment planning part,
wherein the treatment planning part stores PDD which is the absorbed dose distribution data in the depth direction, which is prepared in advance, by using the absorbed dose at the reference depth which is a predetermined position and nearer to an incident side of the pencil beam than the position of a Bragg peak as the reference, and the irradiation dose set value which is calculated by using an absorbed dose at the reference depth as the reference is outputted to the irradiation dose controller.

2. The particle beam treatment device according to claim 1, wherein the treatment planning part stores the absorbed dose at the reference depth regarding the plural energy of the particle beam and PDD using the reference depth as the reference.

3. The particle beam treatment device according to claim 2, wherein the reference depth is set at a position where the change of the PDD in the depth direction is 5%/mm or less.

4. The particle beam treatment device according to claim 1, wherein the treatment planning part stores PDD which is the absorbed dose distribution data in the depth direction in a phantom which is acquired by using the phantom in advance, by using the absorbed dose at the reference depth which is a predetermined position which is nearer to an incident side of the pencil beam than the position of Bragg peak in the phantom as the reference, and the irradiation dose set value is calculated by using the absorbed dose at the reference depth as the reference so as to output to the irradiation dose controller.

5. The particle beam treatment device according to claim 2, wherein in advance, regarding plural energy of the particle beam, the ratio of total absorbed dose value to total measurement value of each energy is obtained by using total absorbed dose value at the reference depth which is the measurement value when the pencil beam is moved in a predetermined range in the phantom and total measurement value of the dose monitor, is obtained, the obtained ratio is standardized by the ratio of the total absorbed dose value to the total measurement value at the reference energy among the plural energy, the energy correction coefficient of each energy is calculated and the irradiation dose set value is calculated by using the energy correction coefficient.

6. The particle beam treatment device according to claim 5, wherein the irradiation nozzle is configured such that the position of the spot is moved laterally and stepwise by moving the pencil beam laterally and stepwise so as for the particle beam to radiate at plural positions of the spot of the target volume; the treatment planning part stores biology dose data at individual positions of spot, and MU value at each spot, which is a monitor unit value at each spot, is calculated by using RBE which is biology effect ratio and depth coefficient which is the ratio of the absorbed dose at a position of Bragg peak in the PDD which is standardized to the absorbed dose at the reference depth, according to the following equation, MU at each spot=biology dose at each spot position/(RBE×depth coefficient×energy correction coefficient).

7. The particle beam treatment device according to claim 6, wherein the treatment planning part, at a predetermined time point, obtains the monitor calibration constant which is the ratio of total absorbed dose value at the reference depth to total measurement value of the dose monitor by using total absorbed dose value at the reference depth and total measurement value in the dose monitor which are the measurement values when the pencil beam of the reference energy is moved stepwise in a predetermined range so as to radiate in the phantom, and calculates the monitor correction coefficient based on the obtained monitor calibration constant, and calculates the irradiation dose set value of each spot based on the monitor correction coefficient and MU at each spot.

8. An irradiation dose setting method of the particle beam treatment device which calculates an irradiation dose set value, in a scanning irradiation in which a spot of a particle beam which is the maximum adsorption region at a position in the depth direction of a target volume which is determined by the energy of the particle beam is formed by radiating the particle beam as a pencil beam to the target volume, and the particle beam is radiated to the target volume by moving the pencil beam in the lateral direction which is perpendicular to the advancing direction so as to move the position of the spot in the lateral direction, wherein a step of storing PDD, which is the absorbed dose distribution data in the depth direction, which is prepared in advance, among the plural energy of the particle beam by using the absorbed dose at the reference depth which is a predetermined position and nearer to an incident side of the pencil beam than the position of Bragg peak as the reference, and a step of calculating the irradiation dose set value based on the PDD which is stored using the absorbed dose at the reference depth as reference are included.

9. The irradiation dose setting method of the particle beam treatment device according to claim 8, wherein a step of acquiring PDD, using a phantom, which is the data of absorbed dose distribution in the depth direction in the phantom at the plural energy of the particle beam is included.

10. The irradiation dose setting method of the particle beam treatment device according to claim 8, wherein a step of obtaining total absorbed value at the reference depth regarding plural energy of the particle beam when the pencil beam is moved in a predetermined range in the phantom, obtaining the ratio of the total absorbed dose value of each energy to total measured value of dose monitor which measures the dose of the particle beam of the pencil beam, standardizing the obtained ratio by the ratio of the total absorbed dose value at the reference energy among the plural energy to the total measurement value, and calculating the energy correction coefficient of each energy.

11. The irradiation dose setting method of the particle beam treatment device according to claim 10, wherein the scanning irradiation is the scanning irradiation in which the pencil beam is moved laterally and stepwise so as to move the position of the spot laterally and stepwise and radiate the particle beams to the plural positions of spot of the target volume, and a step of calculating MU of each spot which is monitor unit at each spot by using biology dose at each spot, RBE which is biological effect ratio, the depth coefficient which is the ratio of the absorbed dose at a position of Bragg peak of PDD which is stored using the absorbed dose at the reference depth as the reference to the absorbed dose at the reference depth and the energy correction coefficient, according to the following equation, MU of each spot=biology dose at each spot position/(RBE×depth coefficient×energy correction coefficient).

12. The irradiation dose setting method of the particle beam treatment device according to claim 11, wherein a step of calculating a monitor correction coefficient based on a calibration constant which is the ratio of total absorbed dose value at the reference depth to total measurement value of the dose monitor at a predetermined time point when the pencil beam of the reference energy is moved stepwise in a predetermined range in the phantom so as to radiate the pencil beam, and calculating the irradiation dose set value of the each spot based on the monitor correction coefficient and MU of each spot.

* * * * *